United States Patent [19]
Ravreby

[11] 3,990,683
[45] Nov. 9, 1976

[54] PACKAGING MEANS

[75] Inventor: Fred A. Ravreby, Framingham, Mass.

[73] Assignee: Reichhold Chemicals, Inc., White Plains, N.Y.

[22] Filed: Dec. 24, 1974

[21] Appl. No.: 536,255

[52] U.S. Cl. .................................. 259/48; 206/219
[51] Int. Cl.² .......................................... B01F 13/00
[58] Field of Search .......................... 259/48, 57, 59; 206/219, 225, 440; 242/71.3

[56] References Cited
UNITED STATES PATENTS

| | | | |
|---|---|---|---|
| 1,070,923 | 8/1913 | Schulz | 206/219 |
| 2,764,157 | 9/1956 | Oliva et al. | 206/221 |
| 3,195,721 | 7/1965 | Weckesser | 206/440 |
| 3,301,252 | 1/1967 | Mahoney, Jr. | 128/90 |
| 3,321,097 | 5/1967 | Soloway | 206/221 |
| 3,521,745 | 7/1970 | Schwartzman | 206/222 |
| 3,630,194 | 12/1971 | Boardman | 128/90 |
| 3,656,475 | 4/1972 | Hanrahan, Jr. | 128/90 |
| 3,679,184 | 7/1972 | Woodham | 206/219 |
| 3,715,189 | 2/1973 | Nighohossian | 206/219 |

FOREIGN PATENTS OR APPLICATIONS

| | | | |
|---|---|---|---|
| 20,896 | 11/1898 | United Kingdom | 259/80 |
| 677,133 | 8/1952 | United Kingdom | 128/90 |

*Primary Examiner*—Peter Feldman
*Assistant Examiner*—Donald B. Massenberg
*Attorney, Agent, or Firm*—Brooks Haidt Haffner & Delahunty

[57] ABSTRACT

Packaging means, especially adapted for packaging a spool of tape and necessary resinforming reactant liquids for making a resin-type orthopedic cast, and for activating the initially separated liquids, applying the mixed liquids by centrifuge on to the tape, and extracting by centrifuge any excess liquid on the tape, all within the unopened package. Package comprises an outer container having a liquid-tight top closure; a container-like partition wall structure nested within and dividing the outer container interior into a lower, "mixing" region and an upper, "wetting and extraction" region; and an inverted cup-shaped rigid inner container within the mixing region for storing one reactant liquid separate from another placed at the bottom of the outer containers. A tape spool is mounted on the partition and within the upper region, and the partition is conical-shaped to funnel the mixed liquid from the mixing region into a hollow core region of the tape spool. A closed upper end of the inner container is press-fit from the underside into the partition wall opening, and a downwardly face open end of the inner container is closed by a valve. A valve stem projects upwardly through the inner container and the package top closure to be pressed downwardly from the package exterior to move the inner container downwardly to open a liquid passage between the upper and lower regions of the outer container, and thereafter open the inner container valve. Fixed mixing paddles ar disposed along the interior bottom periphery of the outer container.

16 Claims, 19 Drawing Figures

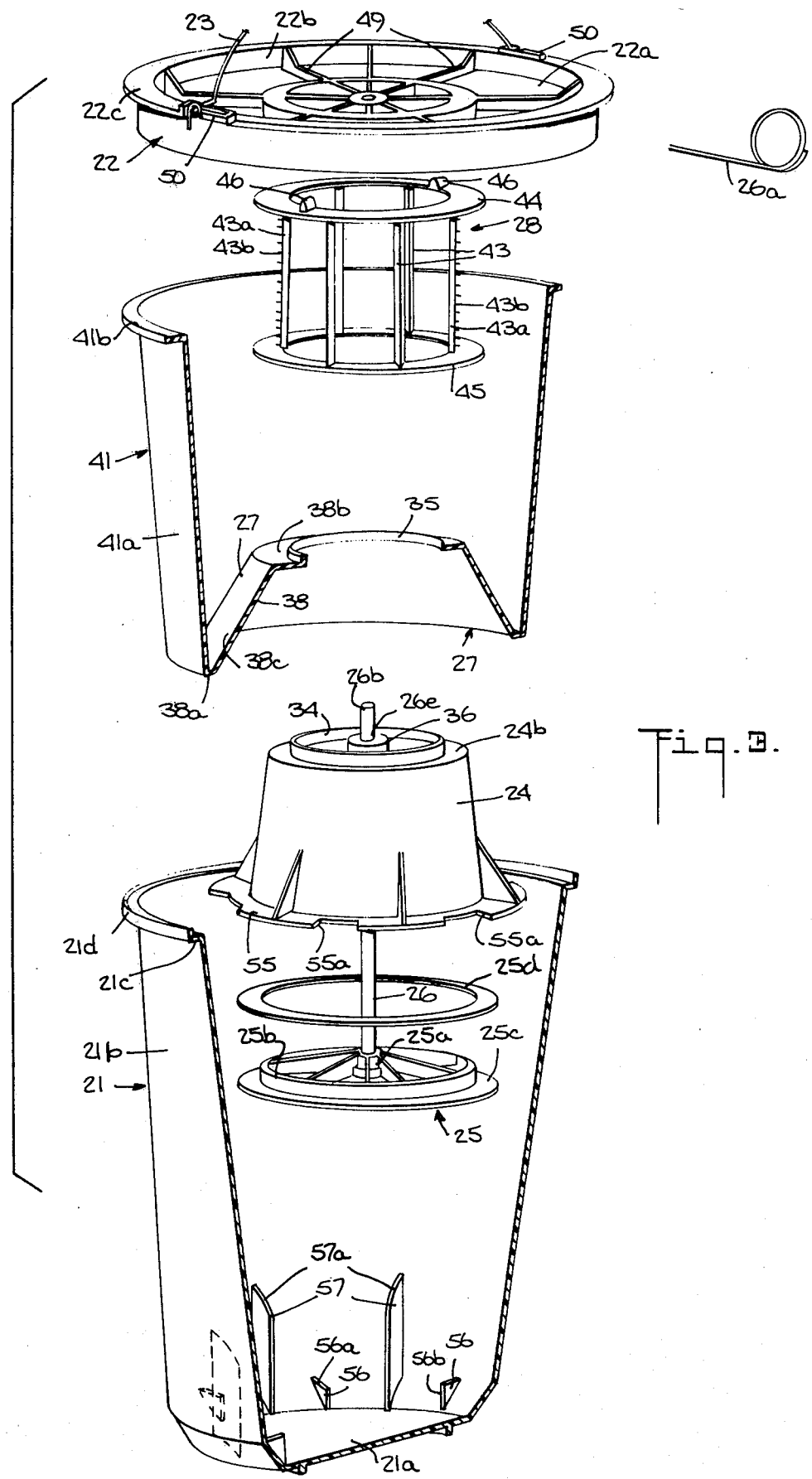

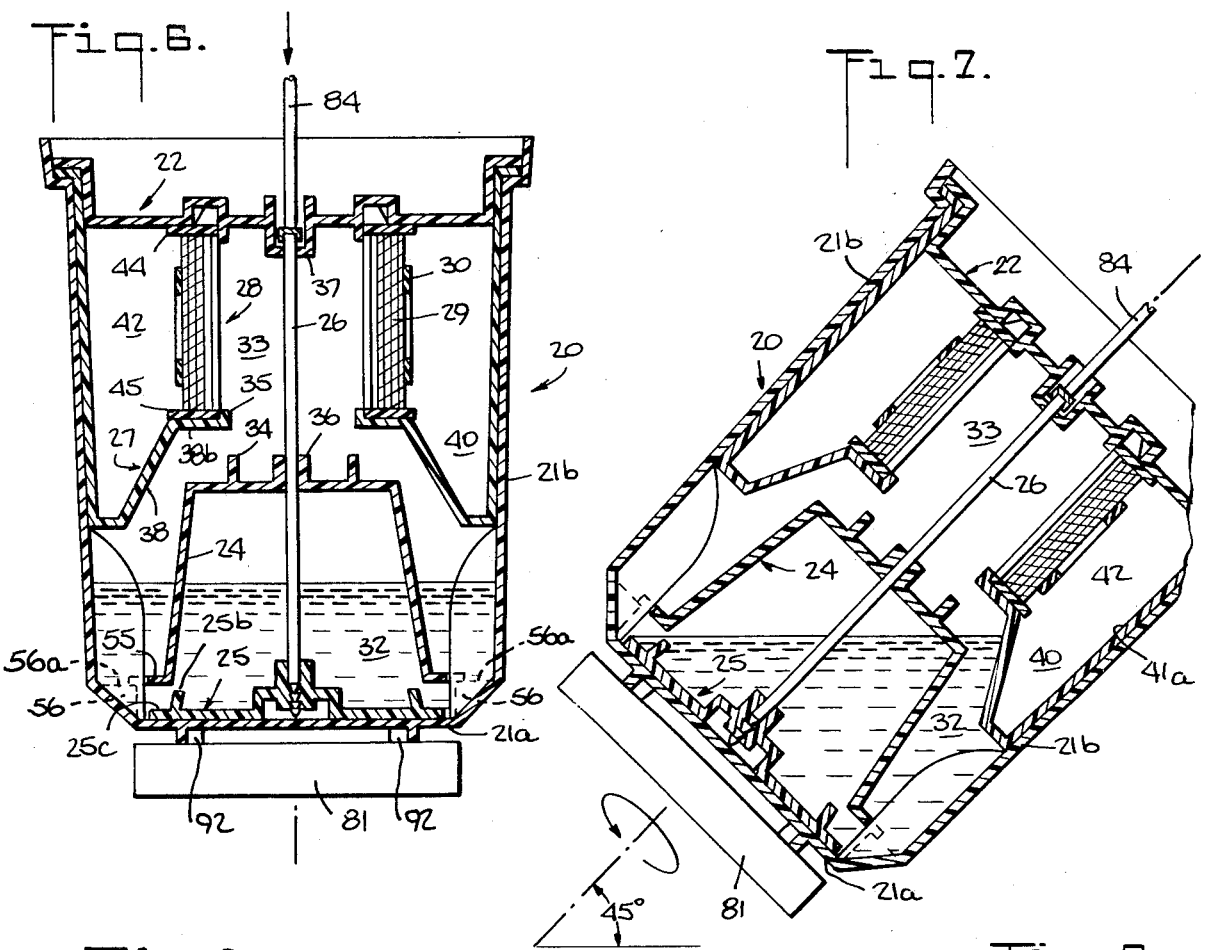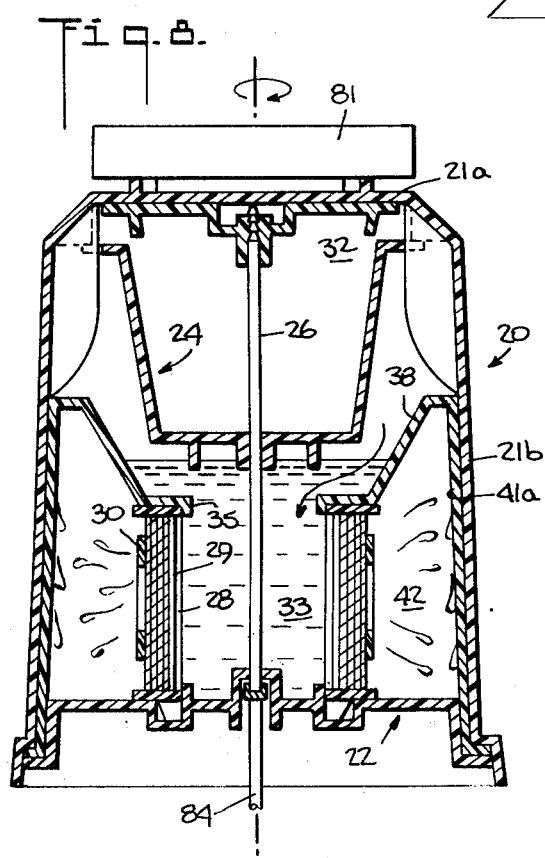

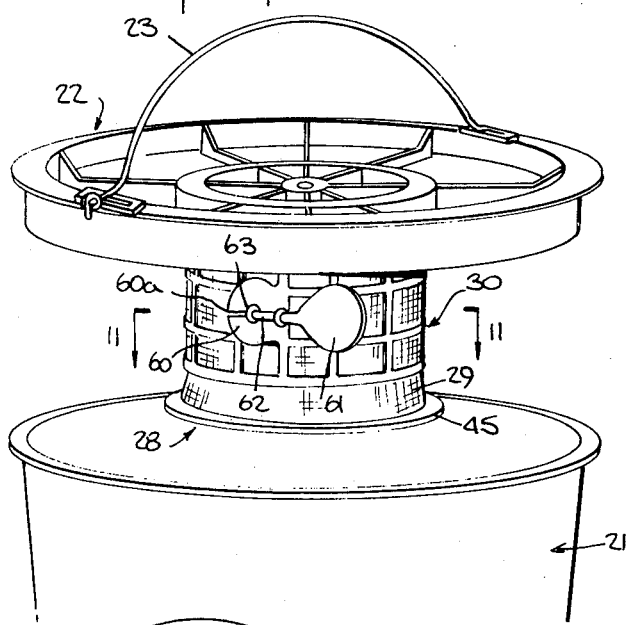
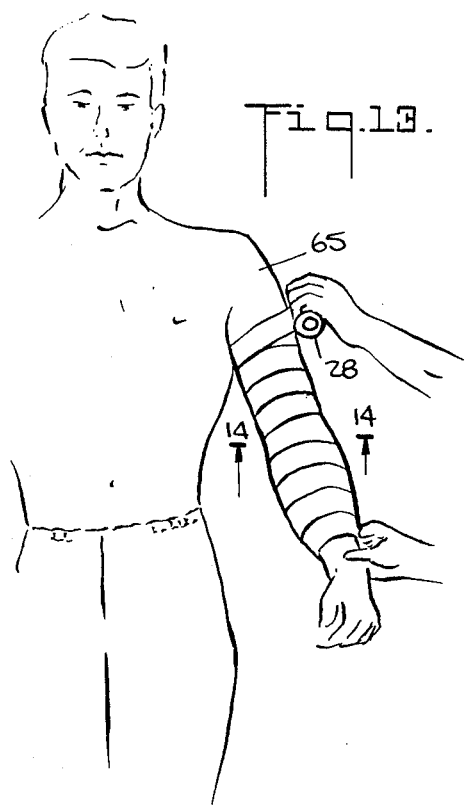
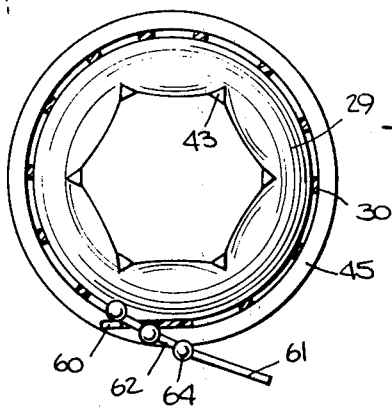
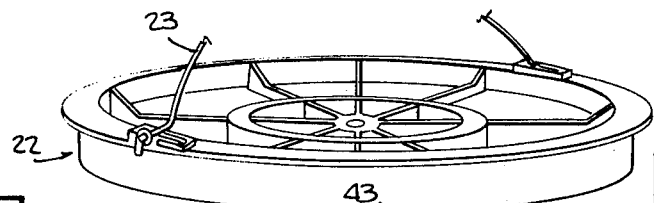
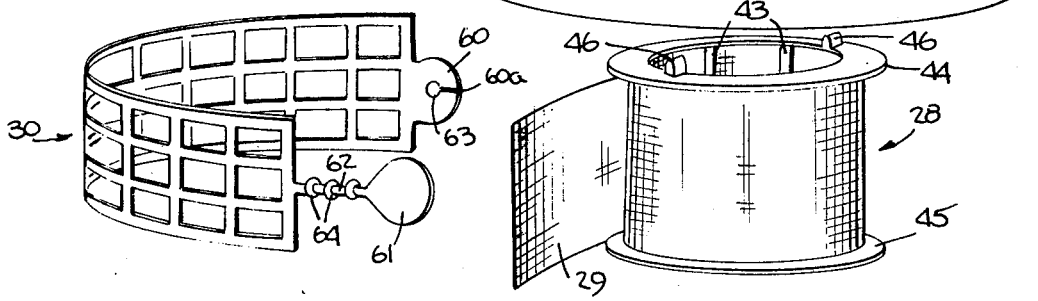
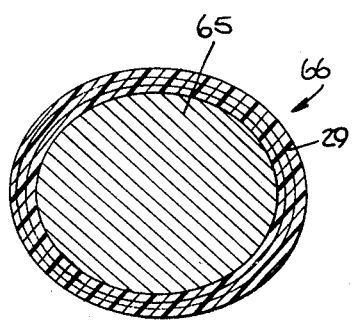

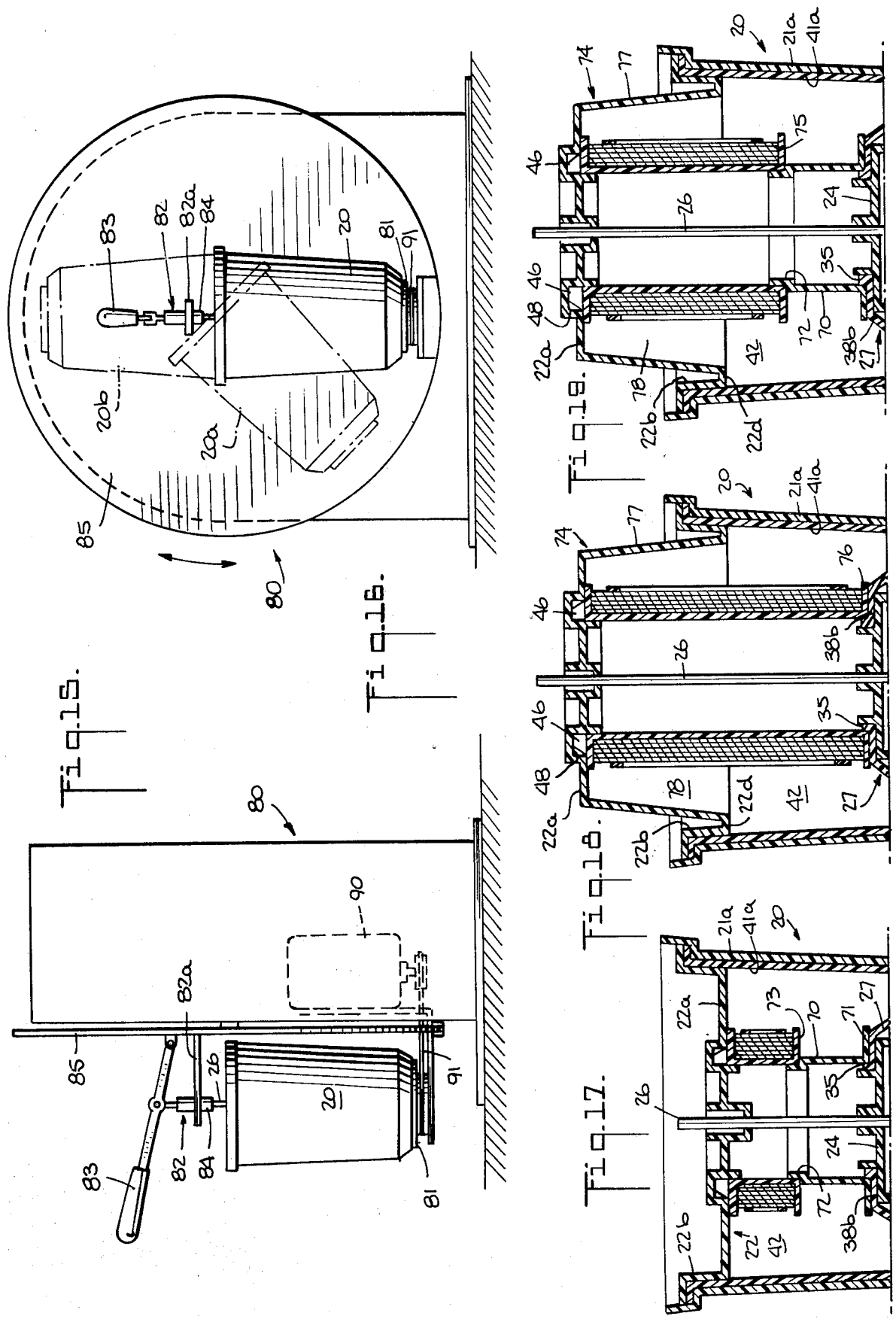

PACKAGING MEANS

This invention relates to packaging means, and more particularly to a compartmented container having features adapting it for separately storing and subsequently mixing together and applying by centrifuge several reactant liquids to a roll of tape material or the like which is stored in a different compartment or region of the package.

Although the invention may have other uses, it was made and will therefore be described in connection with the development of a method and means for packaging and thereafter activating resin-forming materials and subsequently applying the activated materials to a tape for use in forming an orthopedic cast on a body member of a patient, as described and claimed in the copending application of Harold B. Kirkpatrick, Edward C. Distler and Marvin Menzin, Ser. No. 536,253, filed Dec. 24, 1974 entitled "Package and Method for Preparing Orthopedic Cast-Making Materials", a related application being that of Edward C. Distler, Ser. No. 536,243, filed Dec. 24, 1974, entitled "Machine for Preparing Orthopedic Cast-Making Materials", the latter application having been abandoned in favor of continuation-in-part application Ser. No. 604,499, filed Aug. 14, 1975.

Orthopedic casts have been made of various curable foamed and unfoamed resin materials which are activated either prior to or after application to the body member in a variety of ways, the purpose of such so-called "casts" being to overcome the known disadvantages of the more conventional plaster of Paris cast. However, either in the manner in which they must be applied to the body member, or in the characteristics of the resulting orthopedic cast, such techniques as are known for preparing and applying plastic orthopedic castmaking materials are not entirely satisfactory. For example, spraying or coating of the resin-forming chemicals on to a fabric placed on the patient's limb is sometimes messy, and does not approximate the familiar manner of applying plaster casts using a roll of tape whose tension and firmness of application can be more readily controlled by the physician as he wraps the tape on the patient's body. Moreover, where the completed plastic orthopedic cast is to be air-pervious, many of the known techniques for applying the resin-forming materials to a porous or woven base fabric do not ensure that the interstices of the material will not be blocked by the cured resin.

It has therefore been found by the aforementioned joint inventors that a spooled tape may be furnished to the physician for use in forming an orthopedic cast, which he may then wind on the patient in the manner he is accustomed when applying plaster casts, the tape being uniformly coated with an adequate though limited amount of preportioned reactant resin materials which are already activated and therefore in a curing liquid state, so that the curing will be completed at room temperature in a matter of minutes after the cast has been applied. Thus, the physician can control the tension and placement of the tape as it is applied to the patient, after which the cast automatically hardens. All of the necessary resin-forming reactant liquids must be preportioned and packaged together with a spool of tape, also of predetermined length, and delivered in a throw-away container for a single use by the physician.

The resin-forming liquids must be activated immediately before the time of their intended use, and the aforementioned inventors therefore also contemplate that the tape must be properly wetted with the activated reactant liquids while the chemicals and the tape remain within the unopened package. Such is intended as assurance that the tape will be coated properly, and independently of individual skills or training and without possibility for error in either the amount or the proportions of the resin-forming constituents. It also avoids messiness when mixing and using the chemicals.

Such activation and wetting of the tape must be done quickly and conveniently, as well as with reproducible quality. Accordingly, those inventors also contemplate that the storing and mixing together of the reactant liquids should be accomplished within one region of the package, and the wetting of the tape should be performed within a separate region.

In addition, and since a number of packages will be delivered at one time to the physician's office or to a hospital for use at future times, the package must afford long shelf life to the packaged chemicals under usual storage conditions, and must withstand reasonable temperature changes and agitation during shipping.

It is also desired that the actions of mixing the chemicals and wetting the tape will be performed by mounting the package of orthopedic cast-making materials on a relatively inexpensive bench-type machine, such as described in both of the aforementioned patent applications, whose cycles are measured and repetitive, and which will be a part of the standard equipment in hospitals or doctors' offices.

It is therefore intended by this invention to provide a packaging means by which the aforementioned objects will be achieved. That is, it is intended to provide a container or packaging means having features adapting it for the packaging and storing of a tape and resin-forming reactant liquids ultimately to be used for making an orthopedic cast, and within which the initially separated liquids can be mixed within one region, and thereafter applied to a spool of tape by centrifuging the mixed liquid through the tape in another region of the package, all in accordance with a sequence of operations intended to be performed by a package-activator machine on which the package will be mounted.

Containers having particular features for mixing purposes are known, but none proper to have features serving the purposes of the present invention. That is, U.S. Pat. No. 3,321,097 (Solowey) discloses a bottle having compartments in which initially separated ingredients are stored and which may be placed in communication by opening a valve using a valve stem operable from the exterior of the bottle. In U.S. Pat. No. 3,321,917 (DeSanto et al.) one of the components to be mixed is initially contained in a separate interior container-like structure which provides a funnel-shaped partition leading to a narrow mouth opening of the structure at its upper end, the narrow mouth opening being initially closed by a vertically movable valve whose stem is attached to the upper end wall of an outer container. the valve is opened by expanding an accordion-like pleated wall portion of the outer container, which causes the valve stem to move upwardly. The package is then inverted to achieve mixing of a first liquid component contained in the interior container-like structure with another liquid component within the outer container. Neither of these packages or containers includes a tape or tape spool, nor contemplates the mounting or wetting of a roll of tape therein. In these and other respects the container and the package of orthopedic cast-making materials as provided by the present invention appear to be different in overall arrangement and features from any known containers or packages.

Briefly describing the invention, the packaging means includes an outer container whose interior is divided into essentially two regions, i.e., a lower mixing region and an upper wetting and extraction region by an inverted funnel-shaped peripherally extending partition wall formed by the bottom wall portion of a container-like structure which is nested within the outer container. The inverted funnel shape of the partition wall provides a centrally located and circular narrow neck opening at its upper end.

A cage-like cylindrical tape spool, having a predetermined length of woven or knitted fiberglass tape wound thereon, is removably mounted on the underside and centrally of a top closure of the package so that when the top closure is placed on the container, the tape spool will be positioned within the upper region of the container, its height extending between the closure and the upper end of the referred to partition wall member. The longitudinal axis of the spool coincides with that of the container so that the open circular area at the underside of the spool surrounds the narrow neck partition wall opening. Thus, when the container is inverted, liquid initially within the lower region will pour through the partition wall opening into the core of the tape and, when the container is subsequently spun on its central axis as will be described, the liquid will be centrifuged through the cagelike tape spool and liquid-pervious tape material, thereby wetting the tape with the liquid. The tape spool is formed by a plurality of annularly spaced apart, slender and flexible rods which do not interfere with the centrifuging liquid and which also flex, as will be described, to avoid open gaps at the top and bottom edges of the wound tape.

The outer diameter of the spool of tape is smaller than the inner diameter of the surrounding container structure thus providing a peripherally extending collection region for excess liquid centrifuged through the tape. When the container is subsequently uprighted and again spun on its axis, any excess liquid within the tape which would otherwise span across and close the interstices of the tape material is extracted by centrifugal action and is initially deposited on the container wall which defines this peripheral liquid collection region. When the spinning is stopped, the extracted excess liquid flows downwardly by gravity on the inner wall surface of the container into a V-shaped peripheral liquid collection zone formed by the exterior surface of the referred to funnel-shaped partition wall member and the surrounding container surface, to which the outwardly projecting lower end of the partition wall member extends.

The package further includes an inner container in which a measured quantity of one of the reactant liquids of the polymer system is stored before mixing with a second reactant liquid at the bottom of the outer container. The inner container is a rigid, inverted cup-like container placed within the mixing region and having a ring-shaped flange on its inverted bottom wall which is press-fit within, and from the underside of the aforementioned narrow neck opening of the partion wall. The open mouth of this inner container, which faces downwardly, functions as a valve seat and is closed by a flat, valve-like closure which is press-fit into the open mouth to form a liquid-tight seal. To further ensure against leakage, a gasket initially wetted with the second reactant liquid is disposed between the valve and the seat.

The inner container valve is opened by downward movement of a valve stem or package activator rod. The rod passes through the inverted bottom of the inner container, thence through the core region of the cylindrical tape spool, and through the top closure on the outer container, so that the rod projects exteriorly and may be operated by pressing it downwardly from the exterior of the package to open the valve on the inner container. The rod fits tightly as it passes through the bottom of the inner container and through the outer container closure, thus providing liquid-tight seals at these locations.

The downward movement of the valve stem rod will be effected by a manually operated toggle clamp on the activator machine on which the package is mounted when an orthopedic cast is to be made. The container will be placed on a spin table of the machine, and pressed downwardly thereagainst by the referred to toggle clamp which engages the top of the upwardly projecting valve stem rod.

Upon opening the inner container valve the contained reactant is released to flow to the bottom of the outer container, to mix with the second reactant liquid. After thorough mixing of these liquids on the activator machine, the package will be inverted by the machine so that the mixed liquids will flow via the aforementioned funnel into the core of the tape spool, and it becomes apparent that the inner container must be removed from its seating engagement within the narrow neck opening of the funnel to permit the liquid to flow therethrough. For this purpose, the relative tightnesses of fits of the valve stem rod, the inner container valve, and the inner container bottom ring within their respective openings are made such that, upon downward movement of the valve stem rod, the still closed inner container will be unseated first, and moved downwardly away from the funnel neck opening to open the latter. During the downward movement an outwardly projecting peripheral rim on the downwardly facing end of the inner container abuts against several upwardly projecting and annularly spaced apart stops at the bottom of the outer container so that further downward movement of the valve stem rod forces the inner container valve to open.

In view of the subsequent centrifuge wetting and extracting operations which will also be conducted on the activator machine, the entire package will be rotated, preferably intermittently, on its longitudinal axis to mix the reactants. To assist this mixing action the interior of the outer container adjacent to its bottom end has fixed, annularly spaced apart, vertical paddles over which the mixing liquids will course during mixing rotation of the package. Spinning of the package during the mixing step is conducted while the central longitudinal axis of the package is tilted at an oblique anole to the horizontal, preferably 45°, such tilting also being done by the activator machine.

After mixing, the activator machine automatically increases the tilt angle to 180°, in which the package is inverted, so that the mixed liquids flow by gravity through the funnel and into the core area of the cylindrical tape spool, as aforesaid. The machine then spins the package at high speed, centrifuging the liquid through the liquid-pervious tape material. After such wetting of the tape the machine automatically returns the package to its upright position, in which it is again spun at high speed to extract by centrifugal action any excess liquid within the interstices of the tape material.

The package is then removed from the machine, and its top closure is opened, whereupon the wetted tape is ready for use. The tape spool has a press-fit connection to the underside of the closure so that the spool is lifted out of the container as its closure is removed. The spool may remain on the closure or be separated therefrom for use, as desired.

These and other objects, features and advantages of the invention will become more apparent from the following detailed description of the invention, when taken together with the accompanying drawings, in which:

FIG. 1 is a perspective showing of an orthopedic cast-making package employing packaging means in accordance with the invention;

FIG. 2 is an enlarged cross-sectional view of the package as seen from lines 2—2 of FIG. 1 showing the container and its contents;

FIG. 3 is a fragmentary and perspective exploded view showing the container components, to further illustrate their details;

FIGS. 4 and 5 are enlarged fragmentary showings, partially in cross section, to illustrate a feature of the container of FIGS. 1–3;

FIGS. 6–9 are cross-sectional showings of handling and method steps to which the package will be subjected when preparing a tape within the package for use in making an orthopedic cast;

FIG. 10 is a perspective showing of the prepared tape as it is being removed from the package;

FIG. 11 is a cross-sectional view of the wetted spool of tape as seen from lines 11—11 of FIG. 10;

FIG. 12 is an exploded perspective showing of the spooled tape and closure sub-assembly in the package;

FIG. 13 is an illustration of how an orthopedic cast is formed using the wetted spool of tape taken from the package;

FIG. 14 is an enlarged cross-sectional showing of an orthopedic cast on a body member, as made using tape prepared in a packaging means in accordance with the invention;

FIG. 15 is a side-elevational view, to a reduced scale, showing how a package embodying the invention is activated on an activator machine;

FIG. 16 is a front elevational view of the machine of FIG. 15, showing the several tilt positions of the package during activation; and FIGS. 17, 18 and 19 are respective fragmentary cross-sectional view of several modified forms of packaging means in accordance with the invention for accommodating various tape sizes.

Referring first to FIGS. 1–3, an orthopedic castmaking package, containing all of the necessary materials for making a resin-type cast, is indicated by reference numeral 20. FIGS. 1 and 2 show the package and its contents as delivered to a hospital or physician's office for later use in making only one cast, after which the container and any residue are discarded. As previously noted, the package will remain closed, even while its contents are being activated and readied for use, and will be opened when it is time to form the cast on the patient.

The cast will be formed by winding a bandage or tape onto the body member of the patient, the tape being damp with the resin-forming liquid materials which are already activated and which will continue to cure in air at room temperature during the several minutes it takes to form the cast, after which the polymerizing liquid will harden, and rigidify the tape and thus the cast. The preferred reactant constituents of a two-component resin system for the purpose are methylene diphenyl diisocyanate modified to remain in the liquid phase at room temperature (77° F.), such as Isonate 143-L made by The Upjohn Company of Kalamzoo, Mich., and a polyol such as Polylite 34-402 made by Reichhold Chemicals, Inc. of White Plains, N.Y., and which is a polyhydric alcohol. The proportions of these reactant monomers are 100 parts by weight of the diisocyanate to 50 parts by weight of the polyol. Dibutyl phthalate, such as 48-550 also made by Reichhold Chemicals, Inc., in the amount of 50 parts by weight is added to the polyol, although all or any portion of this plasticizer could be added to the diisocyanate coponent. The catalyst is dibutyl tin dilaurate, such as T-12 made by M&T Chemicals Co. Division of American Can Company, New York, N.Y., and is added to the polyol component in an amount ranging from about 0.03 to about 0.30, preferably 0.06 parts by weight. Thus, in the preferred embodiment in which all of the plasticizer is contained in the polyol, the ratio of the diisocyanate material to the polyol and plasticizer material is about 1:1 by weight.

The tape which will be wetted with the reacting monomers is preferably of knitted or woven material, so that the cast will be air-permeable when formed. The preferred tape material is made of interlaced glass yarns which are first desized and then coated with a coupling agent or finish, such as the material described in U.S. Pat. No. 3,793,686 (Nisbet et al.) and obtainable from Carolina Narrow Fabric Co. of Winston-Salem, N.C.

The total amount of reactant liquid materials A and B which will be contained in the package 20 depends, of course, upon the length and width, and to some extent the absorbency, of the tape to be contained in the package. For example, the package 20 to be described in connection with FIGS. 1–16 contains a 5-foot length of nominally 2 inch wide (actual dimension 1¾ inch) tape of the type described, and the package 20 contains a total of about 5 fluid ounces of the reactant liquids A and B, which provides an excess quantity of liquid to ensure that the tape is thoroughly wetted without recycling any centrigued excess liquid back to the core of the tape spool during the contemplated centrifuge wetting operation.

Referring again to the drawings, FIGS. 2 and 3 show that the package 20 has an outer container 21 having a top closure 22 which has a handle 23; an inverted cup-like inner container 24 having a valve 25 which normally closes its downwardly facing open end 24a; a vertically movable valve stem 26 for opening the valve 25, the stem having a removable cotter pin 26a; a partition wall member 27; and a tape spool 28; which together serve as a packaging means for the materials for making an orthopedic cast. The cast-making materials are the two reactant liquid materials A and B of the resin system and the length of tape 29 which is wound on the tape spool 28. The packaging means also includes a plastic mesh retainer band 30 (see also FIGS. 10–12) which holds the wound tape 29 in place.

The materials from which these packaging components are made are such as will not be attached by the constituents of the reactant liquids A or B, particularly the diisocyanate. Preferably, and excepting for the valve stem 25 and handle 23 which are made of metal, they are all of polypropylene or other ethylene plastic material.

The reactant liquids A and B, which will react and begin to polymerize when mixed together, are stored separately within the package, at least one of them being in a liquid-tight compartment. In the embodiment shown, reactant material A is packaged in the liquid-tight enclosure 31 formed by the interior of the inner container 24 and its normally closed valve 25, and reactant material B is placed in the bottom interior region 32 of the outer container 21, adjacent to its bottom wall 21a, such also being a liquid-tight enclosure as will be seen. The reactant liquids A and B are admixed by unseating and opening the valve 25 which normally frictionally engages and seals the inner container open end 24a whereupon the liquid A flows into the liquid B. The valve 25 is opened by downward movement of the valve stem 26, after removal of the cotter pin 26a, and it will be noted that the polymerizing reaction is initiated from the exterior of the package 20 in view of the exteror projection, above the top closure 22, of the upper end 26b of the valve stem 26. Hence, the valve stem 26 may also be referred to as the package activator rod.

After the reactant liquids A and B have been mixed in the lower region 32, the package 20 will be inverted so as to pour the mixed and now curing liquid into the hollow core region 33 of the cylindrical tape spool 28, whereupon the package will be spun in the inverted position to centrifuge the liquid through the tape spool 28 and tape 29 to completely wet the latter therewith. However, by comparison of FIGS. 2 and 3 is will be understood that the upwardly facing closed end wall 24b of the inner container 24 has an axially projecting annular sealing ring 34 which is frictionally received within a comating aperture formed by a flanged rim 35 of the partition wall member 27, and it will be noted that inner container 24 must be moved away from such seating engagement in order to open the narrow neck central aperture of the partition wall member 27 to permit the liquid to pass therethrough and into the spool core region 33. It will also be noted that the valve stem rod 26, which is attached as by serrations 26c at its lower end 26d to a central boss 25a of the valve 25, passes through an apertured central boss or collar 26 at the center of the inner container end wall 24b. The valve stem 26 extends upwardly therefrom through a central collar 37 of the top closure 22, with which it has a sliding, though liquid-tight fit. Thus, although in order to open the valve 25 the valve stem 26 must slide through the inner container closed end collar 36, the valve stem has a friction fit within the collar 36 which is tighter than the friction fit between the inner container annular ring 34 and the partition wall flanged rim 35 so that, upon downward movement of the valve stem 26 in response to pressure on its upper end 26b, the entire inner chamber 24 will be moved downwardly out of engagement with the partition wall member 27 before the inner container valve 25 is opened. Thus, liquid flow communication between the lower region 32 of the outer container and the spool core region 33 is established before the valve 25 is opened.

It will also be noted that the partition wall member 27 includes an inverted funnel-shaped wall portion 38 which widens in the downward direction and includes an outwardly projecting peripheral portion 38a which engages the interior periphery of the side wall 21b of the outer container 21, and at its upper end 38b supports the tape spool 28. Thus, the outer surface 38c of the funnel-shaped portion 38, together with the substantially cylindrical surrounding container structure which extends upwardly from the outer periphery of the lower projecting portion 38a, forms a substnatially V-shaped excess liquid collecting region 40 for receiving the excess of the centrifuged liquid reactant material, as will be further described.

Rather than forming the partition wall member 27 integrally with the side wall 21b of the outer container 21, it is actually formed by the lower end wall of a container-like partition structure 41 whose upwardly projecting side wall 41a lies contiguously against the inner surface of the outer container side wall 21b and whose outwardly projecting peripheral rim 41b at its upper open end seats against the similarly projecting mouth rim 21c of the outer container 21. Thus, the position of the wall portion 38 is fixed, as intended. Along the outer periphery of the outer container rim 21c is an upwardly extending peripheral portion 21d which guards the top cover 22, handle 23, and cotter pin 26a against premature displacement. Thus, in the preferred embodiment, the outer periphery of the excess liquid collection region is actually defined by the interior surface of the partition wall structure side wall 41a, although the wall portion 41a substantially coincides with the interior of the side wall 21b of the outer container 21.

Completing the description of the top closure 22 and the tape spool 28, FIG. 2 shows that the tape spool extends between the horizontal annular ring portion 38b of the partition wall member 27 and the underside of the top closure 22, thus forming a peripherally extending liquid extraction region 42 surrounding the tape spool and tape 29 in view of the smaller diameter of the tape spool 28 as compared with the diameter of the peripherally surrounding container side wall 41a.

Referring to FIG. 3 the tape spool 28 has cylindrical cage-like structure defined by the several narrow and parallel, annularly spaced apart, flexible cage rods 43 which extend between the flat upper and lower end flanges or rings 44, 45 along their interior circumferences. Of course, a suitable mesh-like structure might be substituted for the cylindrically arranged cage rods 43. Two opposed cage rods 43a have a plurality of outwardly projecting thicket-like prongs 43b along their lengths to facilitate retention of the tape 29 on the tape spool.

The height of the spool 38 measured between its end rings 44 and 45 is made the same (i.e., 1¾) as the width of the tape 29 wound thereon. Upon winding the tape it will be found that the slender and therefore very flexible plastic rods 43, 43a will bow inwardly under the tape-winding pressure, resulting in a shortening of the overall height of the spool between these flanges in the amount of one-sixteenth inch or more. Such shortening of the height of the spool 28 relative to the width of the tape has the beneficial effect of closing any otherwise existing gaps at the top and bottom edges of the tape as they conjoin with the inwardly facing surfaces of the spool rings 44, 45 to prevent the centrifuging liquid from bypassing the tape material at these locations.

Projecting above the upper end ring 44 of the tape spool 28 is an opposed pair of cover connection pieces 46 which slidably engage a downwardly projecting central annular ring 47 (FIG. 2) at the underside of the cover 22 to center the tape spool 28 at the underside of the cover. The annular ring 47 of the closure 22 forms the inner sidewall of an upwardly projecting annular channel area 48 of the closure, within which the closure connection pieces 46 of the tape spool are received, as will also be understood from FIG. 2. The outer sidewall 47a of the channel 48 frictionally engages the lower ends of the tapered outer edges 46a of the connection pieces 46 to secure a press-fit removable connection between the closure and the spool for ultimate removal of the latter with the closure when the package is opened. The underside of the tape spool 28 as defined by its end ring 45, slidably surrounds the narrow neck aperture defining ring 35 of the partition wall member 27 to prevent liquid flow between the spool and partition, yet not interfere with removal of the tape spool from the package.

The otherwise flat central area 22a of the closure 22 is reinforced, as by radial gussets 49, against flexure, and has an upwardly projecting peripheral rim 22b which fits snugly within the open mouth of the wall structure member 41, as also seen in FIG. 2. The closure 22 also has an outwardly projecting peripheral rim 22c which seats against the similar rim 41b of the wall structure member 41 and which, together with the snug fit at the rim 22b, forms a liquid-tight seal.

As best seen in FIGS. 4 and 5, the outwardly projecting peripheral rim 22c of the closure 22 includes opposed, reinforced handle receiving structures 50, one on each side of the closure, each including a radially outward projecting handle pivot pin 51 on which the respective end loops 23a of a substantially C-shaped handle 23 are mounted. Each handle loop 23a is a single loop from the outwide towards the inside of the closure 22 as shown, and includes a tangential lever extension portion 23b at its free end. When the pivotable handle 23 is lying flat against the cover 22 when the package is closed as seen in FIGS. 1 and 2, the tangential lever extension 23b lies flat against the outwardly projecting peripheral rim 41b, each of the handle receiving structures 50 being displaced upwardly as at upward recesses 52 to receive the extensions 23b, and apertured as at 52a to accommodate the handle loops 23a, as best seen in FIGS. 2 and 4. Referring to FIGS. 4 and 5, the lengths of the lever extensions 23b are greater than the vertical height between the rim 41b and the top of the outer container peripheral rim 21d so that, when the handle is lifted in the direction of the arrow in FIG. 5 the extensions 23b act as levers to loosen and lift the closure 22 straight up and out of its snug fit engagement within the mouth of the container.

Returning now to the manner in which the valve 25 is opened to permit the reactant liquid A in the inner container 24 to admix with the reactant liquid B, a comparison of FIGS. 2 and 6 shows that after the downward movement of the valve stem 26 has disengaged the inner container 24 from the partition wall aperture ring 35 as previously described, an outwardly extending peripheral rim 55 which surrounds the downwardly facing open end 24a of the inner container 24 abuts against the upper edges 56a of a series of annularly spaced apart support ledges 56 which project upwardly from the outer container bottom wall 21a and radially inwardly from the upwardly projecting peripheral sidewall 21b, whereupon further downward movement of the valve stem 26 unseats the valve 25 from its snug fitting engagement within the mouth of the inner container 24.

Regarding the seating of the valve 25, the valve has an annularly extending and upwardly projecting conical retainer ring 25b whose upwardly and inwardly tapered exterior peripheral surface fits snugly within the mouth formed by the comating oppositely tapered interior peripheral surface at the downwardly facing open end 24a, and an outwardly projecting portion 25c of the valve preferably carries a gasket 25d which seats against the adjacent rim 55 of the inner container 24, thus forming a liquid-tight seal. The gasket 25d is made of thin, liquid-pervious or absorbent material, such as filter paper and, prior to its placement and the closing of the container 24 with reactant liquid A therein, the gasket is dampened with reactant liquid B (or any reactant liquid which will react with and polymerize upon contact with liquid A) so that any liquid A as would otherwise leak through the valve will react with the liquid in the gasket and thereupon polymerize, thus sealing the valve.

Regarding the manner in which the valve 25 opens, it will be noted that the diameter of the valve periphery 25c is smaller than the diametral spacing between the vertical inner edges 56b of any two opposed support ledges 56 so that it moves freely past these edges.

To assist the mixing action of the reactant liquids as will take place within its lower region 32, the outer container 21 further includes integrally formed and radially inward projecting vertical paddles 57, these being annularly spaced apart and located alternately between the support ledges 56, as best seen in FIG. 3. As shown in FIGS. 2 and 3, the outwardly projecting lower rim 55 of the inner container 24 is notched, as at 55a at each peripheral location therealong corresponding to the location of a paddle 57 along the interior of the outer container sidewall 21b so that the inner container 24 is free to move vertically with respect to the paddles 57, but not in circumferential direction with respect thereto. It will be noted that the paddles 57 are parallel to the central longitudinal axis of the package 20, substantially between the bottom wall 21a of the outer container and the partition wall 27. The paddles have arcuately shaped upper end edges 57a.

As illustrated in FIG. 7, mixing of the reactant liquids within the region 32 is performed by intermittently rotating the package 20 about its central longitudinal axis while the axis is tilted at an oblique angle, preferably 45°, to the horizontal. Although the mixing might be done at slower rotational speeds, it has been found that from about 6 to about 16 (depending upon the composition of the reactants) spinning bursts of short duration, perhaps 1 to 2 seconds, on a spin table designed to achieve 2200 r.p.m. but which, because of the short time duration, never achieves such rated speed, causes thorough mixing of the reactants. Tilting of the package and the presence of paddles 57 prevent centrifugal hang-up of the liquid, and assist the mixing action.

After mixing is completed so that the polymerizing reaction has commenced, the mixing spin cycle is stopped and the still unopened package 20 is further tilted to the 180° position in which it is inverted as illustrated in FIG. 8, whereupon the mixed liquid flows via the funnel 38 through the narrow neck partition wall opening formed by the funnel neck ring 35, and into the core region 33 of the cylindrical tape spool 28. After a few seconds to permit such flow, the package 20 is again spun on its central axis, this time at 2200 r.p.m. for about 5 seconds, which causes the liquid within the core region 33 to be centrifuged through the interstices of both the tape spool 28 and the liquid-pervious tape material 29 to thoroughly and uniformly wet the tape 29. To ensure thorough wetting an excess of liquid is provided, much of which emerges from the outer periphery of the spool of tape into the extraction region 42 therearound. However, some liquid may remain within the core region 33 of the tape spool.

After the wetting step the spinning is stopped and the package is uprighted as shown in FIG. 9, in which position it is permitted to remain stationary for a few seconds to permit draining of any liquid from the tape spool core region 33 back through the funnel opening 35 to the bottom of the outer container 21 where it collects, and to permit downward draining of the excess liquid from the peripheral wall 41a and the underside of the cover 22 into the excess liquid collection region 40. The package is then spun at 2200 r.p.m. on its central axis to remove by centrifugal extraction any excess liquid remaining within the tape 29 as would otherwise seal the interstices of the tape material. Such excess liquid is also initially deposited on the peripheral wall 41a and, after the spinning has stopped, will also collect in the liquid collection region 40.

After such extraction, the liquid impregnated or coated tape material is damp to the touch, and is ready for winding on the patient's body member to form an orthopedic cast. As previously noted, the liquid is in a curing state, and will harden within about 10 minutes.

Referring briefly again to FIGS. 4 and 5, the package 20 is now opened by lifting and pivoting the handle 23 about the pivot pins 51 to remove the top closure 22 as previously described. As illustrated in FIG. 10, the removed closure carries with it the now wetted spool of tape 29.

Referring to FIGS. 10-12, the plastic mesh tape retaining band 30 has at one of its ends a slotted eyelet piece 60, the slot being indicated by reference numeral 60a, by which it is connected to its opposite end which carries the finger tab 61 and includes a rod-like adjustment length portion 62 which is received in the eyelet 63 of the eyelet piece 60, via the slot 60a. The tightness of the band 30 around the spool of tape 29 is adjustable by appropriate selection and engagement of one of the knobs 64, which are integrally formed on the rod-like extension 62 and have diameter larger than the eyelet 63.

When the wetted spool of tape has been removed from the package as shown in FIG. 10 the tape spool 28 may be separated from the cover 22 by grasping its lower flange ring 45, the cover 22 continuing to be held in the other hand. The physician first removes band 30 by grasping the finger tab 61 and pulling the extension portion 62 back through the eyelet slot 60a. As illustrated in FIG. 13, the physician then winds the wetted tape on a body member of the patient, such as his arm 65, applying the tape directly from the spool 28. As illustrated in FIG. 14, it is believed that winding to provide three layers of the tape on the patient's limb will be adequate to form an extremely effective orthopedic cast 66. Although not illustrated, it should be understood that the patient's body member will be initially covered with a knitted sleeve or the like, so that the resin does not contact his skin.

Referring now to FIGS. 17-19, it is shown that, by using several differently configured top closures with or without a spacer spool 70 (FIGS. 17 and 19), and by lengthening the valve stem 26 if necessary (FIGS. 18 and 19), the same package 20 may accommodate tapes of different widths. That is, as previously mentioned, the tape spool 28 illustrated in FIG. 2 has 2 inch wide tape wound thereon. If a 1 inch wide tape is to be packaged, FIG. 17 illustrates that the same top closure 22 would be used, but that a nominally 1 inch wide (i.e., 1 inch high) spacer spool 70, having a lower end ring 71 to be received over the partition wall ring 35 and an upper end ring 72 whose exterior diameter is the same as that of the wall ring 35, would be interposed between the underside of the 1 inch tape spool 73 and the partition wall portion 38b.

A high crown closure 74 as illustrated in FIGS. 18 and 19 is substituted for the closure 22 when either a 3 inch wide tape (FIG. 19) or a 4 inch wide tape (FIG. 18) is to be packaged. In FIG. 19, the underside 75 of the 3 inch high tape spool is seated on the upper end ring 72 of the spacer spool 70 whereas, as shown in FIG. 18 no spacer is needed for the 4 inch high tape spool whose lower end ring 76 engages the wall ring 35 and is seated directly on the partition wall portion 38b, as in the FIG. 2 embodiment.

Excepting for its 2 inch higher central crown portion 77, the high crown closure 74 has substantially the same features as the closure 22. That is, it has a flat, though narrower central portion 22a and an upwardly projecting annular channel ring 48 into which the cover connection pieces 46 of the 1 inch, 3 inch and 4 inch tape spools are snugly received as previously described, and the closure 74 has a substantially vertical peripheral rim 22b which fits within the open mouth at the upper end of the wall partition structure 41, as in the case of closure 22. Although not illustrated, the high crown closure 74 has a semi-circular handle 23, including a convenient closure removal feature similar to that shown in FIGS. 4 and 5. Moreover, it should be noted that upwardly projecting peripheral wall of the crown portion 77 has a diameter substantially larger than that of the 3 inch and 4 inch high tape spools in order to provide an excess liquid extraction region 78 within the crown, which is an upward continuation of the extraction region 42 within the upper region of the package above the partition wall 27. As shown in either of FIGS. 18 or 19, the high crown wall portion 77 projects upwardly from the lower end 22d of the peripheral rim 22b.

As previously described in connection with FIGS. 6-9, the orthopedic cast-making package 20 is intended to be activated on the scene, where the patient is being treated. Accordingly, it is contemplated that the activating steps previously described will be performed on the package by an activator machine, such as the machine 80 which is diagrammatically illustrated in FIGS. 15 and 16, and which would be available as a part of the general equipment of the hospital or physician's office.

Briefly, and referring first to FIG. 15, the package 20 is placed on a spin table 81 of the machine which can be rotated by a spin motor 90 via the pulley belt 91. One or more of an annularly spaced apart plurality of radially inward projecting lugs 92 formed on the bottom wall 21a of the outer container 21 engage one or more upwardly projecting spin lugs 93 of the table 81 to assist the spin engagement between the table and the package. A toggle clamp 82, which is manually operated by the handle 83, presses the package 20 downwardly against the table 81. Excepting for its vertically movable clamping head 84, the clamp 82 is mounted in fixed position on a bracket 82a which projects forwardly from a tilt frame 85 to which the bracket is attached. The spin motor 90 is also mounted on the tilt frame 85, but onits rearward side.

From the position of the clamp 82 in alignment with the upwardly projecting end of the package valve stem 26, it will be understood that downward movement of the clamping head 84 moves the stem 26 downwardly, and activates the package by permitting the reactant liquids A and B to admix with each other. It will also be noted from FIGS. 6–9 that downward clamping of the package against the spin table 81 is actually via the valve stem 26 and opened valve 25 which presses against the bottom wall 21a of the package.

FIG. 16 shows the three positions of the package 20 during the mixing, wetting, and extraction steps, the mixing and tape wetting positions being shown in phantom lines and designated 20a and 20b, respectively. The initial placement position of the package 20 and the same position for the extraction step is shown in full lines. The tilt frame 85 is rotated between these three positions by a tilt motor (not shown), at each of which the tilting is stopped.

Thus has been described a packaging means which achieves all of the objects of the invention.

What is claimed is;

1. Packaging means comprising an outer container having a central longitudinal axis, a bottom wall and a peripheral side wall extending upwardly from said bottom wall and providing an open upper end of said outer container, a top closure, a peripherally extending partition wall member within and dividing said outer container into upper and lower regions, said partition wall member having an upper end and a lower end and including a lower end peripheral portion extending outwardly substantially to an adjacent peripheral interior surface portion of said side wall of the outer container and a conical wall portion tapering inwardly towards said upper end of the partition wall member and defining a narrow neck opening of the partition wall member providing a liquid flow passage between said upper and lower regions of the outer container, means separate from said partition wall member providing a rigid, liquid-tight inner container mounted within said lower region of the outer container beneath said narrow neck opening of the partition wall member and spaced upwardly from said bottom wall of the outer container, said inner container having a closed upper end and a downwardly facing open end, valve means normally closing said open end of the inner container, and valve stem means on said valve means and extending upwardly therefrom and being slidable through said closed upper end of the inner container and through said top closure for opening said inner container valve from the exterior of said outer container.

2. Packaging means according to claim 1 which further comprises fixed mixing paddle means within said lower region of the outer container.

3. Packaging means according to claim 1 which further comprises tape spool means removably mounted on said top closure to project downwardly therefrom into said upper region of the outer container and having a longitudinal axis coinciding with said central longitudinal axis of the outer container, said tape spool means having a lower end surrounding said narrow neck opening of the partition wall member and height extending between said narrow neck opening of the partition wall member and said top closure.

4. Packaging means according to claim 3 wherein said tape spool means comprises a cylindrical cage-like tape spool having a plurality of annularly spaced apart, slender rods defining a cylindrical core region of the spool, the diameter of said spool being substantially smaller than that of said outer container side wall to provide a liquid extraction region between the spool and the sidewall.

5. Packaging means according to claim 4 wherein said tape spool rods are flexible.

6. Packaging means according to claim 4 wherein said top closure has downwardly projecting circular ring means centrally thereof, and said spool further comprises upper end means removably engaging said circular ring means of the top closure.

7. Packaging means according to claim 6 wherein said tape spool means further comprises spacer spool means disposed between said tape spool and said narrow neck opening of the partition wall member, said spacer spool means having means defining a hollow, open-ended but otherwise closed cylindrical core extending therethrough between said neck opening of the partition wall member and said core region of said tape spool.

8. Packaging means according to claim 1 wherein said closed upper end of the inner container is seated against and thereby closes said narrow neck opening of the partition wall member and has engagement means retaining said closed relation with the latter, said valve stem means engaging said closed end of the inner container during said valve opening movement thereof to move said inner container away from, and thereby open said narrow neck opening of the partition wall member, and which further comprises stop means for stopping said movement of said inner container during said valve opening movement of the valve stem means after said neck opening has opened to permit movement of said valve stem means relative to said inner container to thereby open said valve means.

9. Packaging means according to claim 8 wherein said valve means includes a valve disc having engagement means normally press-fit into said open end of the inner container to retain said normally closed condition of the valve, and said stop means comprises a plurality of annularly spaced apart, vertically extending bottom protrusions on said outer container and disposed along the interior periphery thereof, the diameter of said valve disc being smaller than the diametral distance between substantially opposed ones of said protrusions, and said downwardly facing open end of the inner container having an outwardly projecting peripheral flange whose diameter is larger than said diametral distance between opposed protrusions.

10. Packaging means according to claim 9 which further comprises a plurality of annularly spaced apart, radially inward projecting and vertically extending mixing paddles on the interior of said sidewall of the outer container and substantially adjacent to its said bottom wall, said outwardly projecting peripheral flange of the inner container having means defining corresponding annularly spaced apart notches in slidable relation with the respective of said mixing paddles.

11. Packaging means according to claim 1 wherein said peripherally extending partition wall member is formed by a bottom wall portion of a separate, container-like structure nested within said outer container, said container-like structure having a peripheral wall portion extending upwardly from its said bottom wall portion and providing an open upper end of the structure, and peripheral rim means engaging said open upper end of the outer container.

12. Packaging means according to claim 11 wherein said top closure comprises a peripherally extending vertical rim seated against, and thereby providing a liquid-tight seal within said peripheral wall portion of said container-like structure at its said open upper end.

13. Packaging means according to claim 12 wherein said top closure vertical rim has an upper end and a lower end, and said top closure further comprises a peripheral wall portion spaced inwardly and extending upwardly from said lower end of the vertical rim, said peripheral wall portion having an upper end and height greater than said vertical rim, and a substantially flat central portion closing said upper end of the peripheral wall portion, and which further comprises a cylindrical cage-like tape spool removably mounted substantially on said top closure central portion to project downwardly therefrom into said upper region of said outer container, the diameter of said spool being substantially smaller than that of said top closure peripheral wall portion to provide a liquid extraction region between the spool and the wall portion.

14. Packaging means according to claim 1 which further comprises means providing laterally projecting peripheral rim portions on substantially opposite sides of said open upper end of the outer container, laterally projecting handle pivot means on substantially opposite sides of said top closure and respectively spaced above said opposite peripheral rim portions of the outer container upper end, and handle means mounted for pivotal movement on said handle pivot means and including respective lever portions adjacent to said handle pivot means, said lever portions having length to engage their respectively associated outer container peripheral rim portions responsive to pivotal movement of said handle means.

15. Packaging means according to claim 1 wherein said inner container contains a quantity of a first reactant resin-forming liquid, said outer container contains a quantity of a second reactant resin-forming liquid for reacting with the first said liquid to form a resin, and said valve means includes a gasket of liquid-pervious material wetted with a liquid which will react and polymerize upon contact with said first reactant resin-forming liquid.

16. Packaging means according to claim 15 wherein said gasket material is wetted with said second reactant resin-forming liquid.

* * * * *